(12) United States Patent
Zoabi et al.

(10) Patent No.: US 10,660,707 B2
(45) Date of Patent: May 26, 2020

(54) ENT BONE DISTANCE COLOR CODED FACE MAPS

(71) Applicant: Biosense Webster (Israel) Ltd., Yokneam (IL)

(72) Inventors: Akram Zoabi, Kfar Masser (IL); Fady Massarwi, Baka al Gharbiyya (IL); Lior Zar, Poria Illit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 36 days.

(21) Appl. No.: 15/847,646

(22) Filed: Dec. 19, 2017

(65) Prior Publication Data
US 2019/0183578 A1 Jun. 20, 2019

(51) Int. Cl.
*G06K 9/00* (2006.01)
*A61B 34/10* (2016.01)
(Continued)

(52) U.S. Cl.
CPC .............. *A61B 34/10* (2016.02); *A61B 6/461* (2013.01); *A61B 6/5217* (2013.01); *A61B 90/37* (2016.02); *G06T 7/11* (2017.01); *G06T 7/187* (2017.01); *G06T 7/60* (2013.01); *G06T 7/73* (2017.01); *G06T 11/001* (2013.01); *G06T 19/20* (2013.01); *A61B 6/03* (2013.01); *A61B 17/24* (2013.01); *A61B 34/20* (2016.02); *A61B 2034/105* (2016.02); *A61B 2034/2051* (2016.02);
(Continued)

(58) Field of Classification Search
CPC ......... A61B 34/10; A61B 90/37; A61B 34/20; A61B 2034/2051; A61B 2090/367; A61B 2090/3762; A61B 17/24; G06T 7/187; G06T 7/11; G06T 7/60; G06T 11/001; G06T 2034/105; G06T 2207/10024; G06T 2207/10081; G06T 2207/30008; G06T 2207/30

See application file for complete search history.

(56) References Cited

U.S. PATENT DOCUMENTS 5,335,173 A 8/1994 Sasahara
5,813,984 A 9/1998 Haaga et al.
(Continued)

FOREIGN PATENT DOCUMENTS

EP 0581704 B1 2/1994
EP 2837328 A1 2/2015

OTHER PUBLICATIONS

Beyer, Johanna, et al. "High-quality multimodal volume rendering for preoperative planning of neurosurgical interventions." *IEEE Transactions on Visualization and Computer Graphics* 13.6 (2007): 1696-1703.
(Continued)

*Primary Examiner* — Xin Jia
(74) *Attorney, Agent, or Firm* — Frost Brown Todd LLC

(57) ABSTRACT

A method includes receiving a computerized tomography (CT) image comprising voxels of a body part of a subject, segmenting the image so as to identify a surface of a skin and a surface of a bone in the image, measuring respective minimum distances to the bone from a plurality of points on the surface of the skin, and rendering an image of the surface of the skin while visually coding the rendered image so as to indicate the respective minimum distances.

21 Claims, 9 Drawing Sheets

(51) Int. Cl.

| | | |
|---|---|---|
| *G06T 11/00* | (2006.01) | |
| *A61B 6/00* | (2006.01) | |
| *G06T 19/20* | (2011.01) | |
| *G06T 7/73* | (2017.01) | |
| *A61B 90/00* | (2016.01) | |
| *G06T 7/187* | (2017.01) | |
| *G06T 7/11* | (2017.01) | |
| *G06T 7/60* | (2017.01) | |
| *A61B 34/20* | (2016.01) | |
| *A61B 34/00* | (2016.01) | |
| *A61B 6/03* | (2006.01) | |
| *A61B 17/24* | (2006.01) | |

(52) U.S. Cl.
CPC ............... *A61B 2034/2068* (2016.02); *A61B 2034/2072* (2016.02); *A61B 2034/254* (2016.02); *A61B 2090/367* (2016.02); *A61B 2090/3762* (2016.02); *G06T 2207/10024* (2013.01); *G06T 2207/10081* (2013.01); *G06T 2207/20101* (2013.01); *G06T 2207/30008* (2013.01); *G06T 2207/30088* (2013.01); *G06T 2210/41* (2013.01); *G06T 2219/2012* (2013.01)

(56) References Cited

U.S. PATENT DOCUMENTS

| | | |
|---|---|---|
| 6,081,739 A | 6/2000 | Lemchen |
| 6,524,250 B1 | 2/2003 | Weber et al. |
| 2012/0230566 A1 | 9/2012 | Dean et al. |
| 2015/0018698 A1 | 1/2015 | Safran et al. |
| 2015/0250553 A1* | 9/2015 | Jaramaz ............... G16B 5/00 703/1 |
| 2016/0048944 A1* | 2/2016 | Ashmole ............. A61B 6/032 382/131 |
| 2016/0180520 A1* | 6/2016 | Huo ..................... G06T 7/11 382/131 |
| 2016/0232686 A1* | 8/2016 | Park .................. G06T 11/001 |
| 2017/0056112 A1 | 3/2017 | Gliner et al. |
| 2017/0091994 A1* | 3/2017 | Beeler ................. G06T 17/20 |

OTHER PUBLICATIONS

Swennen, Gwen RJ, Wouter Mollemans, and Filip Schutyser. "Three-dimensional treatment planning of orthognathic surgery in the era of virtual imaging." *Journal of oral and maxillofacial surgery* 67.10 (2009): 2080-2092.

European Communication dated May 23, 2019 for Application No. 18213406.4, 5 pages.

Russian Office Action dated Jun. 20, 2019 for Application No. 2018144110, 6 pages.

Russian Search Report dated Jun. 20, 2019 for Application No. 2018144110, 2 pages.

* cited by examiner

ENT BONE DISTANCE COLOR CODED FACE MAPS

FIELD OF THE INVENTION

The present invention relates generally to image-guided surgery, and particularly to registration between magnetically tracked instruments and computerized tomography (CT) images.

BACKGROUND

In image-guided surgery (IGS) a medical practitioner uses instruments that are tracked in real time so that positions and/or orientations of the instruments may be presented on images of a subject's anatomy during a surgical procedure. In some cases both the tracking and the imaging of the subject's anatomy may be implemented by one modality, such as fluoroscopy. However, because fluoroscopy uses ionizing radiation, its use should be minimized. Consequently in many scenarios an image of the subject is prepared in one modality, such as magnetic resonance imaging (MRI) or computerized tomography (CT) fluoroscopy, and the instrument tracking uses a different modality, such as electromagnetic tracking.

U.S. Pat. No. 5,335,173 describes a medical diagnosis image display method comprising the steps of transforming respective three-dimensional image information on a skull of a subject to be examined and diagnosed and skin covering the outer surface of the skull.

U.S. Pat. No. 6,081,739 describes a conventional digital panoramic radiographic unit, which includes sonic or optical three dimensional scanning detector and a color video detector so that when the panoramic x-ray data is obtained, three dimensional contour of the surface of the subject's skin and the outward visual appearance of the subject's skin are also obtained as correlated data sets.

U.S. Pat. No. 5,813,984 describes a method and device for generating a forensic skull and soft tissue database used for the on-line facial reconstruction of victims and age progression portrait rendering of missing children through utilization of advance diagnostic radiologic modalities.

European Patent EP0581704B1 describes a method for determining the position of an organ of a subject with respect to at least two image-forming devices.

U.S. Pat. No. 6,524,250 describes a device that can be easily used by surgeons to measure and monitor changes before, during, and after a liposuction procedure and assist in producing symmetrical body contours.

SUMMARY

Embodiments of the present invention that are described hereinbelow provide for a method for improved registration between a magnetically tracked surgical instrument and a CT image.

There is therefore provided, in accordance with an embodiment of the present invention, a method including receiving a computerized tomography (CT) image including voxels of a body part of a subject, segmenting the image so as to identify a surface of a skin and a surface of a bone in the image, measuring respective minimum distances to the bone from a plurality of points on the surface of the skin, and rendering an image of the surface of the skin while visually coding the rendered image so as to indicate the respective minimum distances.

In an embodiment visually coding the rendered image includes applying a first image characteristic to first areas of the skin where the minimum distance does not exceed a predetermined threshold, and applying a second image characteristic to second areas of the skin where the minimum distance exceeds the predetermined threshold.

In another embodiment the first and second image characteristics are two distinguishable colors. Alternatively, the first and second image characteristics are two distinguishable patterns. Further alternatively, the first and second image characteristics are two distinguishable graylevels.

In a further embodiment visually coding the rendered image includes applying a first image characteristic to first areas of the image of the surface of the skin where the minimum distance exceeds a predetermined first threshold, applying a second image characteristic to second areas of the image of the surface of the skin where the minimum distance does not exceed a predetermined second threshold, and applying a third image characteristic to third areas of the image of the surface of the skin where the minimum distance does not exceed the first threshold but exceeds the second threshold.

In still another embodiment the first, second, and third image characteristics are three distinguishable colors.

In yet another embodiment the color of the third image characteristic is a combination of the colors of the first and second image characteristics. The relative weights of the first and second colors in the combination are determined from a ratio of a first difference to a second difference, where the first difference is a difference between the first threshold and the minimum distance, and the second difference is a difference between the minimum distance and the second threshold. Alternatively, the first and second image characteristics are two distinguishable graylevels, and the third image characteristic is a third graylevel. The third graylevel is an interpolated graylevel between the graylevels of the first and second image characteristic, where the interpolated graylevel is determined by differences between the minimum distance and the first and second thresholds, respectively.

In another embodiment the body part is a head.

In a further embodiment the minimum distance for each of the plurality of points is established along a normal to the surface of the bone at each of the plurality of points.

There is also provided, in accordance with an embodiment of the present invention, an apparatus including a display device and a processor, which is configured to receive a computerized tomography (CT) image including voxels of a body part of a subject, to segment the image so as to identify a surface of a skin and a surface of a bone in the image, to measure respective minimum distances to the bone from a plurality of points on the surface of the skin, and to render an image of the surface of the skin on the display device while visually coding the rendered image so as to indicate the respective minimum distances.

In an embodiment visually coding the image includes applying a first image characteristic to first areas of the skin where the minimum distance does not exceed a predetermined threshold, and applying a second image characteristic to second areas of the skin where the minimum distance exceeds the predetermined threshold.

In a further embodiment the first and second image characteristics are two distinguishable colors. Alternatively, the first and second image characteristics are two distinguishable patterns. Further alternatively, the first and second image characteristics are two distinguishable graylevels.

In another embodiment visually coding the image includes applying a first image characteristic to first areas of the image of the surface of the skin where the minimum distance exceeds a predetermined first threshold, applying a second image characteristic to second areas of the image of the surface of the skin where the minimum distance does not exceed a predetermined second threshold, and applying a third image characteristic to third areas of the image of the surface of the skin where the minimum distance does not exceed the first threshold but exceeds the second threshold.

In still another embodiment the first, second, and third image characteristics are three distinguishable colors.

In yet another embodiment the color of the third image characteristic is a combination of the colors of the first and second image characteristics. The relative weights of the first and second colors in the combination are determined from a ratio of a first difference to a second difference, where the first difference is a difference between the first threshold and the minimum distance, and the second difference is a difference between the minimum distance and the second threshold. Alternatively, the first and second image characteristics are two distinguishable graylevels, and the third image characteristic is a third graylevel. The third graylevel is an interpolated graylevel between the graylevels of the first and second image characteristic, where the interpolated graylevel is determined by differences between the minimum distance and the first and second thresholds, respectively.

In another embodiment the minimum distance for each of the plurality of points is established along a normal to the surface of the bone at each of the plurality of points.

There is also provided, in accordance with an embodiment of the present invention, a computer software product, including a non-transitory computer-readable medium in which program instructions are stored. The instructions, when read by a computer, cause the computer to receive a computerized tomography (CT) image comprising voxels of a body part of a subject, to segment the image so as to identify a surface of a skin and a surface of a bone in the image, to measure respective minimum distances to the bone from a plurality of points on the surface of the skin, and to render an image of the surface of the skin while visually coding the rendered image so as to indicate the respective minimum distances.

The present invention will be more fully understood from the following detailed description of the embodiments thereof, taken together with the drawings in which:

DETAILED DESCRIPTION OF EMBODIMENTS

Overview

Figure 1:
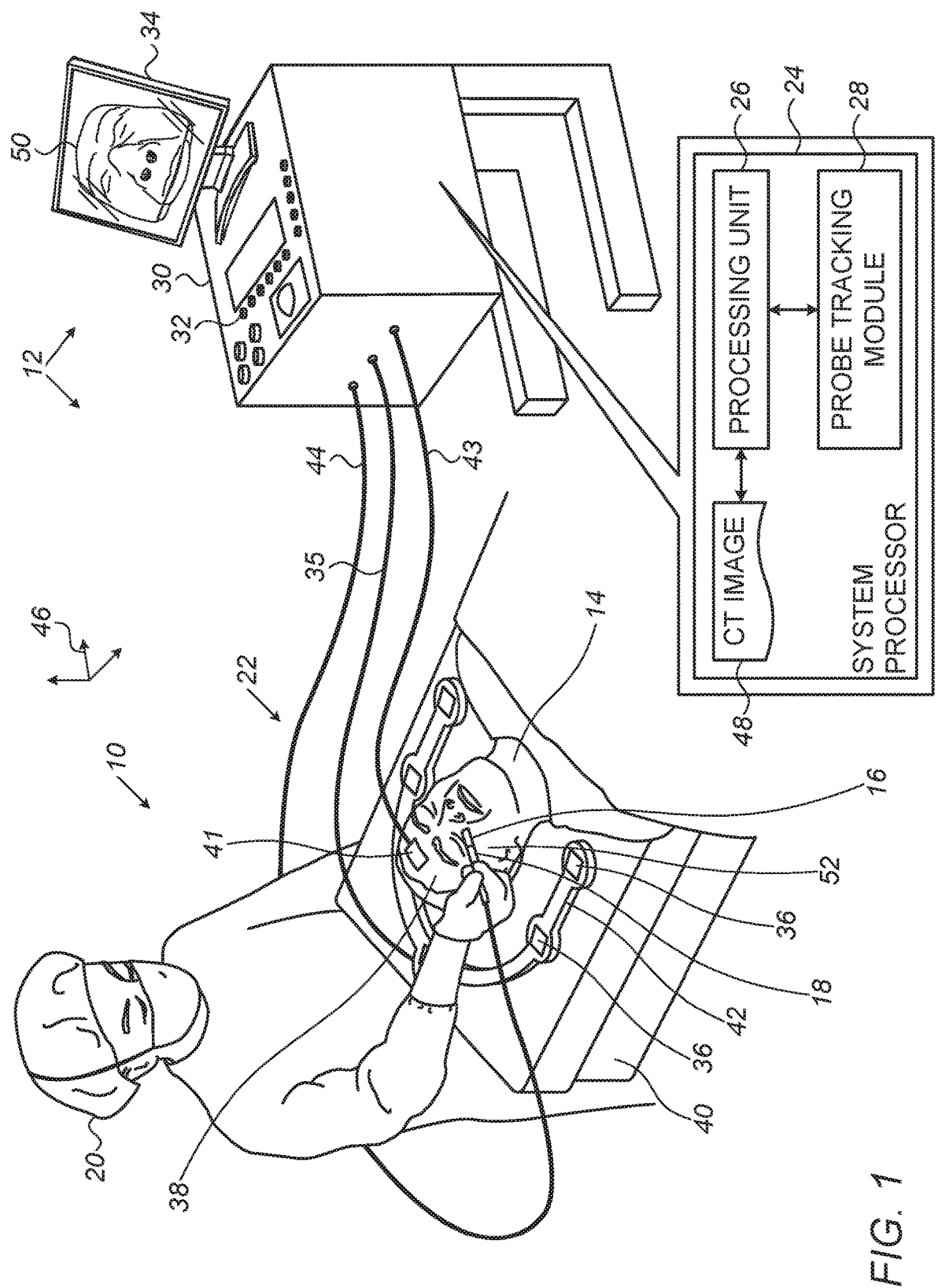
FIG. 1 is a schematic diagram of a surface registration system, according to an embodiment of the present invention.

Determining the location and orientation of a surgical instrument within the body of a subject may be done by utilizing magnetic tracking. In ear, nose, and throat (ENT) surgery, a magnetic tracking system is first registered to the head of the subject. The registration procedure typically utilizes a pre-recorded CT image of the subject's head. In a preliminary phase of the registration procedure, the surgeon touches the subject's face in a few, typically four, points using a wand-like probe assembly carrying a registration probe. The position and orientation of the registration probe is recognized by the magnetic tracking system. Based on these four points, a processor performs an initial registration by fitting, using a registration algorithm, the locations of the points in the magnetic tracking system with their locations in the CT-image.

The resulting registration is typically not yet sufficient for an accurate determination of the location and orientation of the surgical instrument. In a second phase of the registration procedure, the surgeon touches the subject's face with the wand in several points. During this process, the processor iterates and improves the registration based on these additional points on the face, using the registration algorithm.

As the registration algorithm is based on fitting the additional points to the outside (skin) contour of the CT image, any error caused by the surgeon by pressing the wand into soft tissue will cause an error in the registration. An error in the registration, in turn, may be detected by the surgeon only after he has inserted a guide wire within the sinus of the subject and finds a discrepancy between the location of the guide wire as given by the registration algorithm and, for example, his tactile feel of the location.

In this case, the surgeon typically extracts the guide wire and redoes the second phase of the registration, causing a delay in the surgical procedure.

Embodiments of the present invention that are described herein solve this problem by rendering an image of the subject's face, wherein the thickness of the soft tissue on covering the facial bones is represented by a visual coding, such as different colors.

In an embodiment of the present invention, a processor receives a computerized tomography (CT) image comprising voxels of a bodily part of a subject. The processor segments the image so as to identify a surface of a skin and a surface of a bone in the image, and measures respective minimum distances to the bone from a plurality of points on the surface of the skin. The minimum distance corresponds to a distance along a normal to the surface of the bone. The processor then renders an image of the surface of the skin while visually coding the image so as to indicate the respective minimum distances. The image may be presented on a screen to the surgeon operating on the subject.

The visual coding of the image typically comprises applying a first image characteristic, such as a color or shading, to first areas of the skin where the minimum distance does not exceed a predetermined threshold, and applying a second image characteristic, such as another color or shading, to second areas of the skin wherein the minimum distance exceeds the predetermined threshold.

Alternatively, the visual coding of the image comprises applying a first image characteristic, such as a first color or shading, to first areas of the skin where the minimum distance exceeds a predetermined first threshold, applying a second image characteristic, such as a second color or shading, to second areas of the skin wherein the minimum distance does not exceed a predetermined second threshold, and applying a third image characteristic to third areas of the skin. In one embodiment the third image characteristic typically comprises a combination of the first and second image characteristics, wherein relative weights of the first and second image characteristics are determined by interpolation.

Although the embodiment above describes an ENT procedure relating to a subject's head, other embodiments comprise medical procedures applied to other parts of a subject's body.

System Description

FIG. 1 is a schematic diagram of a surface registration system 10, according to an embodiment of the present invention. System 10 is used to register a magnetic tracking system 12 with an image, herein by way of example assumed to comprise a computerized tomography (CT) image, of a subject 14. Tracking system 12 is used to track positions and orientations of one or more instruments, such as catheters or guidewires, that are inserted into subject 14 during a medical procedure performed on the subject. As is described below, tracking system 12 is also able to track the position and orientation of a registration probe 16 that is external to the subject. Probe 16 is fixedly connected to a handle 18 that may be held by a professional 20, typically a surgeon, during use of system 10. The combination of probe 16 and handle 18 form a rigid probe assembly 22 that facilitates the positioning by professional 20 of the probe to a desired location.

For clarity and simplicity in the following description, the medical procedure referred to above is assumed to comprise an invasive procedure on a nasal sinus of subject 14, so that surface registration system 10 and magnetic tracking system 12 are assumed to be configured to operate in and around the region of the nasal sinus. However, it will be understood that systems 10 and 12 may be configured to operate in and around other regions of a subject, such as the kidneys or abdomen, and those having ordinary skill in the art will be able to adapt the description herein for such other regions.

Tracking system 12 is operated by a system processor 24, comprising a processing unit 26 communicating with a probe tracking module 28. The function of module 28 is described below. Processor 24 may be mounted in a console 30, which comprises operating controls 32 that typically include a pointing device such as a mouse or trackball. Professional 20 uses the operating controls to interact with processor 24, which, as described below, may be used to present results produced by systems 10 and 12 to the professional on a display device 34, also referred to herein as screen 34.

Processor 24 uses software stored in a memory of the processor to operate system 10. The software may be downloaded to processor 24 in electronic form, over a network, for example, or it may, alternatively or additionally, be provided and/or stored on non-transitory tangible media, such as magnetic, optical, or electronic memory.

In order to track the instruments referred to above within subject 14, as well as to track probe 16, processing unit 26 uses probe tracking module 28 to operate, via a cable 35, a plurality of magnetic field generators 36, typically coils. In one embodiment, typically applicable if subject 14 is anesthetized and has a recumbent immobile head 38 on a bed 40, generators 36, as illustrated in FIG. 1, are fixed to a frame 42 typically placed on the bed, besides the subject's head. In an alternative embodiment (not shown), applicable if subject 14 is not anesthetized, generators 36 are fixed with respect to each other and to a frame attached to head 38. A three-axis reference coil 41 is fixed to head 38, and connected to processing unit 26 with cable 43.

Generators 36 radiate alternating magnetic fields into and external to head 38 of subject 14, and these fields generate signals in magnetic detectors in the instruments and in probe 16. The signals are conveyed back to processing unit 26 and probe tracking module 28, typically in the case of probe 16 via a cable 44 connecting the probe to console 30, and the processor and the module together analyze the signals to provide locations and orientations of the instruments and probe 16 with respect to generators 36. It will be understood that magnetic field generators 36 define a coordinate frame of reference 46 of magnetic tracking system 12.

The Carto® system, produced by Biosense Webster, of Irvine, Calif., uses a tracking system similar to that described herein to track the location and orientation of the distal tip of a probe inserted into a subject.

System processor 24 stores a digitized CT image 48 of head 38 of subject 14. Digitized CT image 48 may be accessed by processing unit 26 for use in registration of system 10, as well as to generate, inter alia, an image 50 of the subject's head 38 on screen 34. During the process of registration, probe 16 is brought into contact with a surface 52 of subject 14, i.e., into contact with the skin of the subject, so that surface 52 is also referred to herein as skin 52.

Figure 2:
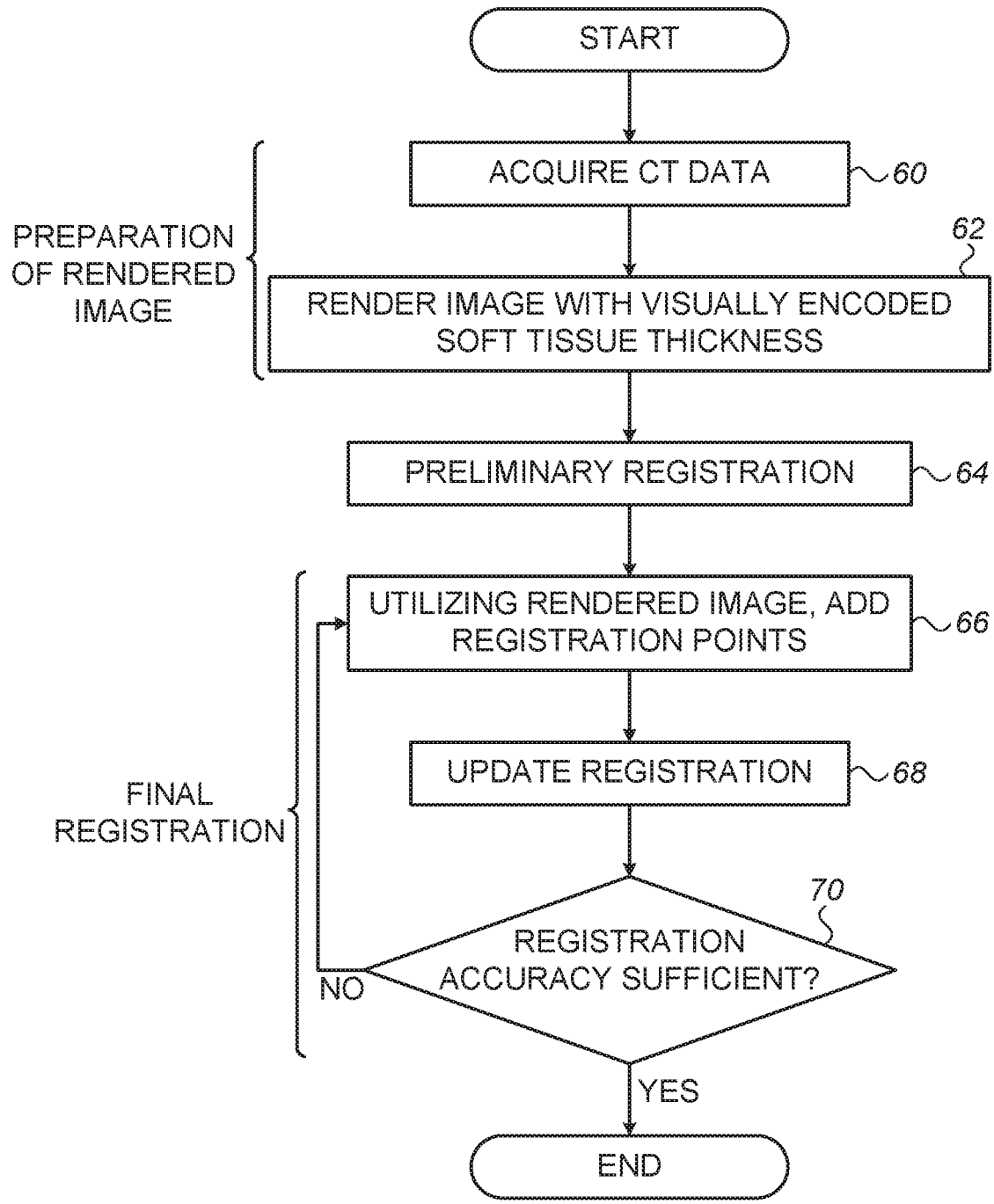
FIG. 2 is a flowchart of a registration process, according to an embodiment of the present invention.

FIG. 2 is a flowchart of a registration process, according to an embodiment of the present invention. An image 94 (shown in FIG. 4) is prepared in a data acquisition step 60 and an image rendering step 62. In data acquisition step 60 CT image 48 is read by system processor 24. Image rendering step 62 is further detailed in the flowchart of FIG. 3 and the description of FIG. 4. In a preliminary registration step 64 CT image 48 and tracking system 12 are registered to each other based on a small number, typically four, of points acquired by professional 20 using rigid probe assembly 22, also referred herein as wand 22, as described with reference to FIG. 5. Final registration comprises acquiring a large number of points in a high-density sampling step 66, an update step 68, and a decision step 70. Steps 66, 68, and 70 are described with reference to FIGS. 6-7.

Figure 3:
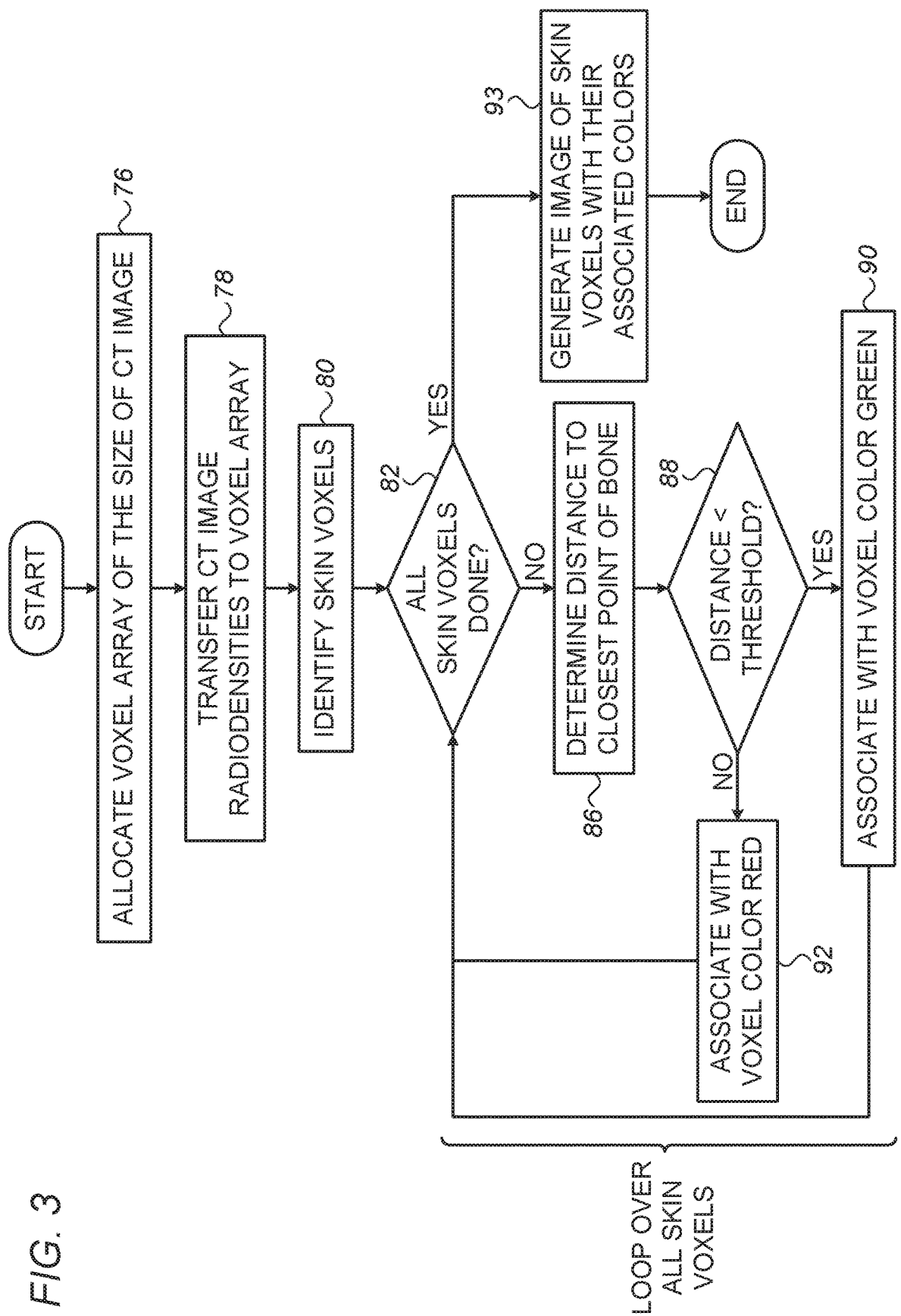
FIG. 3 is a flowchart of the process for rendering an image in an image rendering step, according to an embodiment of the present invention.

FIG. 3 is a flowchart of the process for generating image 94 in image rendering step 62 of FIG. 2, according to an embodiment of the present invention. Image 94 is also referred to herein as rendered image 94. System processor 24 allocates in an allocation step 76 a 3-D data array 77 with the same dimensions as digitized CT image 48, and transfers in a transfer step 78 the CT image into the data array. Each point in data array 77 is called a voxel 79. In an identification step 80, system processor 24 identifies in data array 77 those voxels 79 associated with skin 52 based on the radiodensities associated with each voxel and its surrounding voxels; these voxels are called "skin voxels" 81.

In steps 82-92 system processor 24 loops over all skin voxels 81, determining in a distance step 86 the distance from the skin voxel to the closest point of underlying bone.

In a comparison step 88, system processor 24 compares the determined distance from skin voxel 81 to the bone to a predetermined threshold, with the threshold chosen by professional 20 to be in the range of 0.5-3 mm. The threshold value is assumed to be a minimum acceptable skin-bone distance. If the distance is less than or equal to the threshold, i.e., is less than or equal to the minimum skin-bone distance, a green color is associated with skin voxel 81 in green association step 90. If the distance is more than the threshold, a red color is associated with skin voxel 81 in red association step 92. Once system processor 24 has looped through all skin voxels 81, the process ends by the system processor generating an image of skin voxels 81 with their associated colors in image generation step 93.

Figure 4:
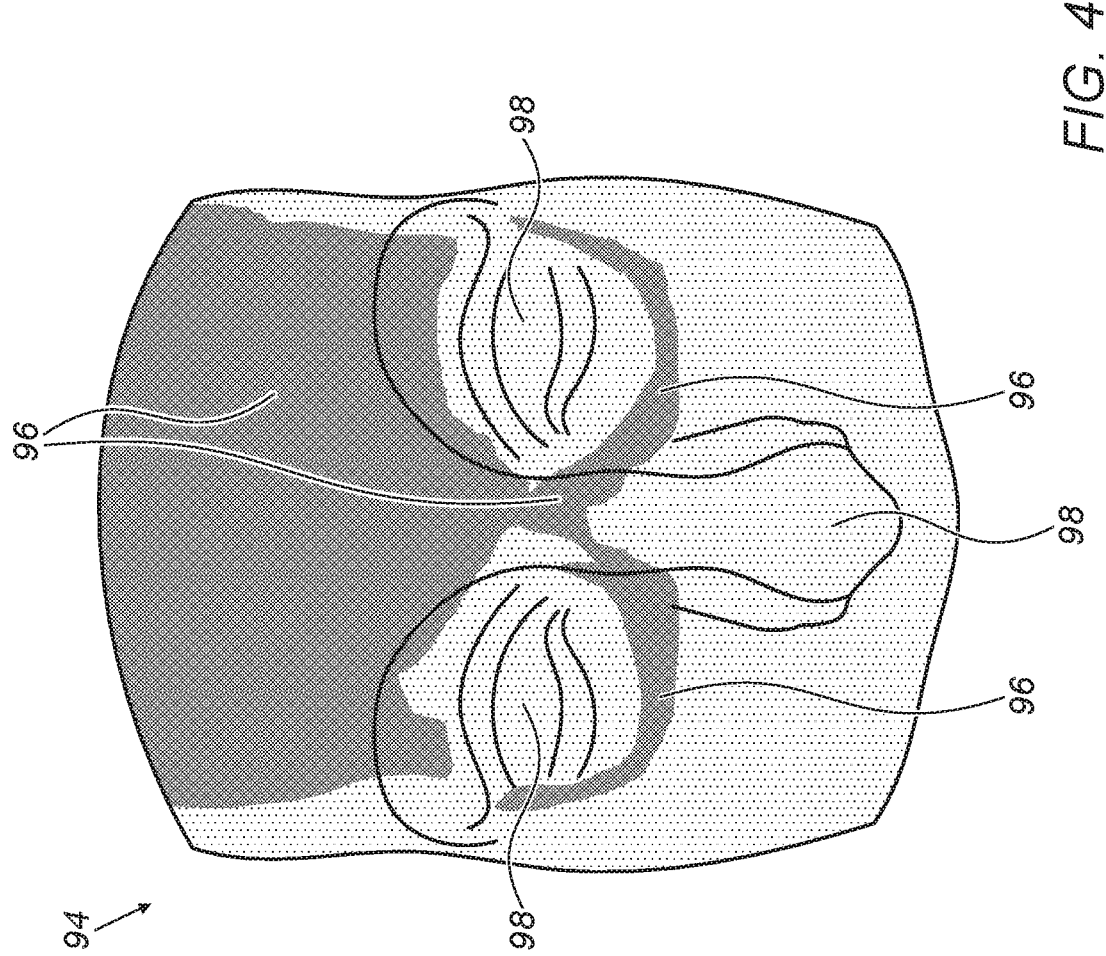
FIG. 4 shows a map indicating the thickness of the soft tissue of the face of a subject, according to an embodiment of the present invention.

FIG. 4 shows image 94 indicating the thickness of the soft tissue of the face of subject 14, according to an embodiment of the present invention. In preparation for the registration between magnetic tracking system 12 and digitized CT image 48, system processor 24 renders image indicating the thickness of the soft tissue, as described below. In the embodiment described hereinbelow the visual coding is based on different colors.

As described above for the flowchart of FIG. 3, system processor 24 identifies in digitized CT image 48 skin voxels 81. For each skin voxel 81, system processor 24 segments CT image 48 to identify bony material of the subject and measures distances from skin 52 to underlying bone. If the distance does not exceed the predetermined threshold, an image of skin voxel 81 on image 94 is colored green. If the distance, however, exceeds the predetermined threshold, the image of skin voxel 81 is colored red. (The colors "green" and "red" are represented in FIG. 4 and subsequent figures by two different shadings as areas 96 and areas 98, respectively.) In the resulting image 94, areas 96 are bony areas wherein the thickness of the soft tissue does not exceed the predetermined threshold, and areas 98 are fleshy areas wherein the thickness of the soft tissue exceeds the threshold.

Although the embodiment described in FIG. 4 uses green and red as the colors for coding image 94, other colors may be used. In other embodiments, more than one predetermined threshold may be used, and each thickness interval between two consecutive thresholds is assigned a different color. In yet other embodiments, a graylevel may be used to indicate the thickness. In still other embodiments, patterning, or combinations of patterning, colors, and graylevels may be used to indicate the thickness.

Figure 5:
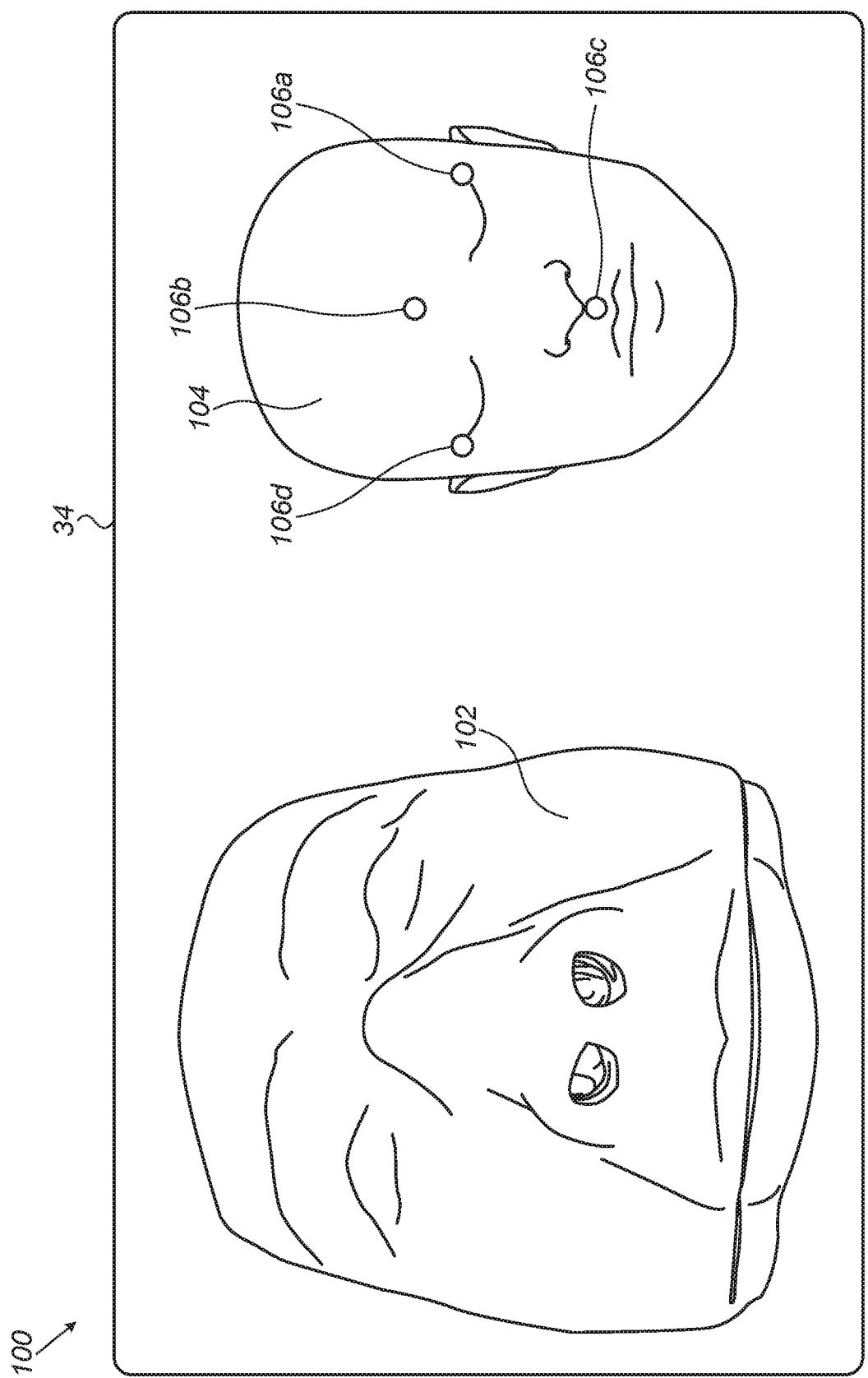
FIG. 5 shows a view on a screen during a preliminary registration, according to an embodiment of the invention.
Figure 6:
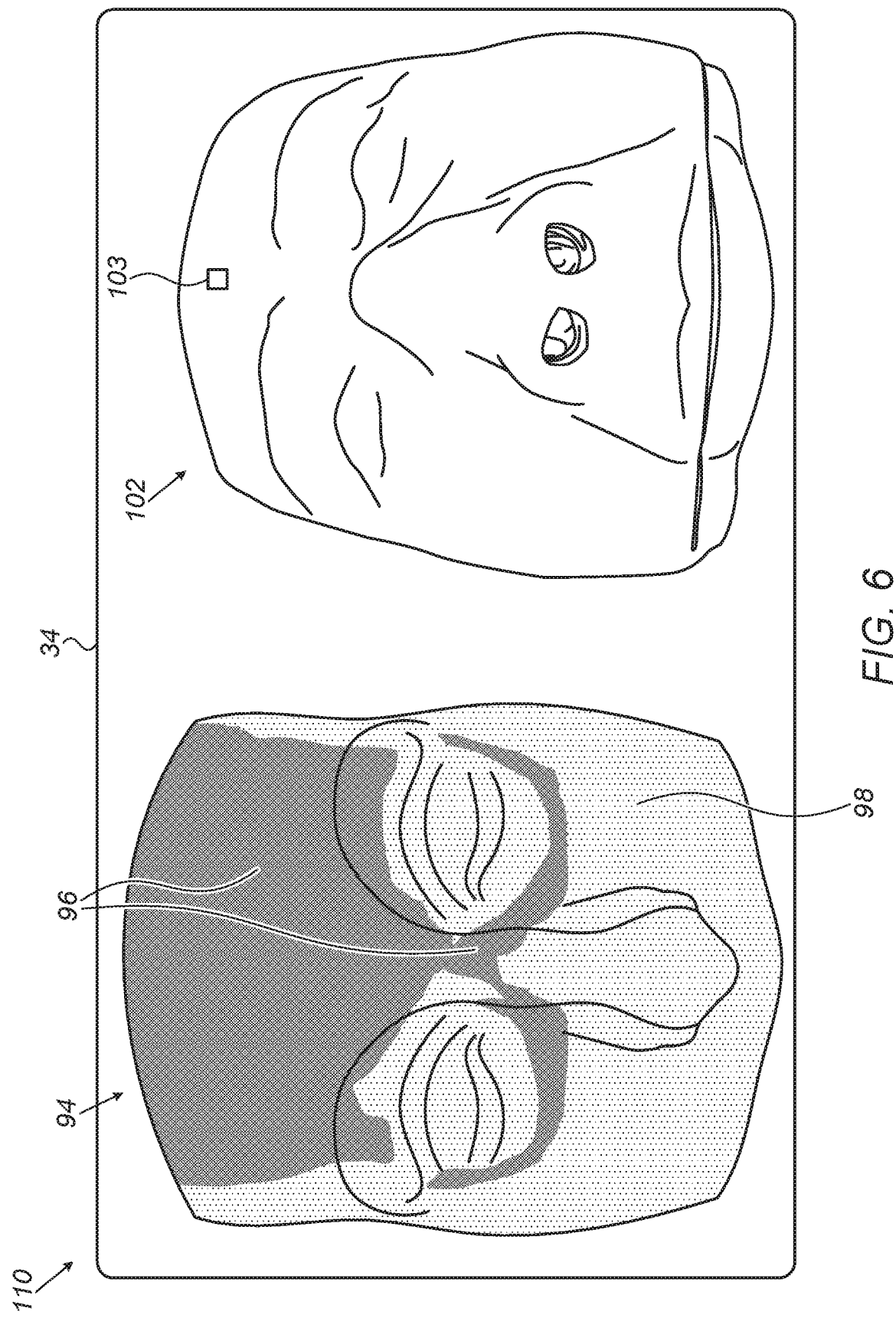
FIG. 6 shows a view on a screen at the start of a final registration according to an embodiment of the invention.
Figure 7:
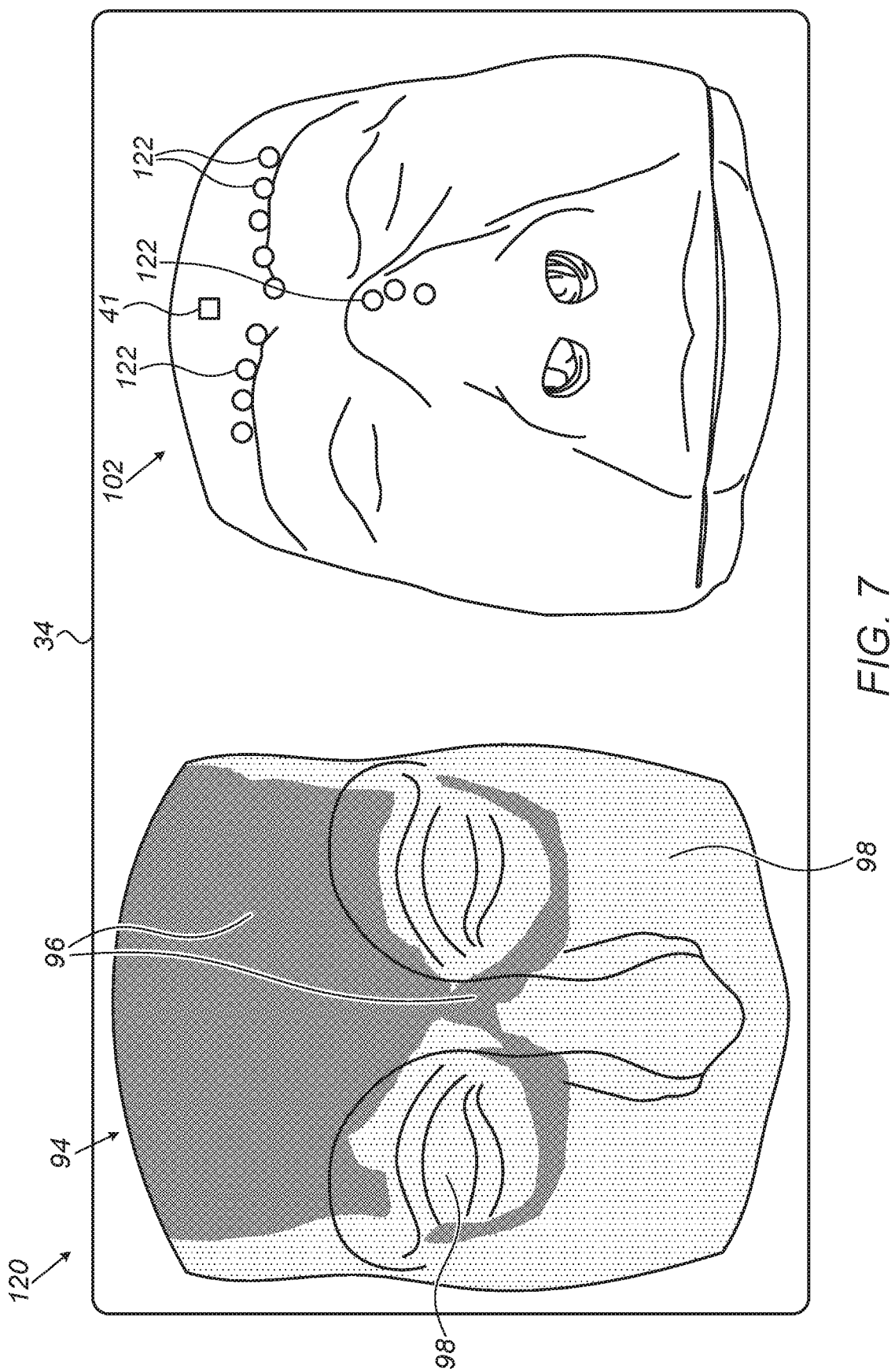
FIG. 7 shows a view on a screen during a final, iterative registration, according to an embodiment of the invention.

FIGS. 5-7 show views on screen 34 during the registration process described by the flowchart of FIG. 2, according to an embodiment of the present invention.

FIG. 5 shows a view 100 on screen 34 during the preliminary registration step 64 (FIG. 2), according to an embodiment of the invention. For the purpose of preliminary registration, system processor 24 displays on screen 34 a face image 102 of subject 14, wherein the face image corresponds to skin 52 of the subject that is extracted from digitized CT image 48 by identifying skin voxels 81. In addition, system processor 24 presents a schematic face representation 104, displaying four points 106a-d. Points 106a-d are locations recommended for the preliminary registration, chosen for their clear locations on a face as well as for bony areas generally found at these locations.

Using probe assembly 22, professional 20 touches with registration probe 16 skin 52 of the face of subject 14 on those four points that, according to the professional's judgement, closest match recommended points 106a-d. Upon touching each of the four points, professional 20 signals to system processor 24, using either controls on probe assembly 22 (controls not shown) or operating controls 32, to record the location and orientation of probe 16.

After recording the location and orientation of probe 16 in the four points, system processor 24 calculates a coordinate transformation between the four points in the coordinate frame of reference 46 of magnetic tracking system 12 and digitized CT image 48 yielding the best spatial fit between the four points and skin voxels 81. This coordinate transformation gives the preliminary registration between magnetic tracking system 12 and digitized CT image 48.

FIG. 6 shows a view 110 on screen 34 at the start of the final registration (described above with regard to the flowchart of FIG. 2), according to an embodiment of the invention. For the purpose of the final registration, system processor 24 displays on screen 34 two images: rendered image 94 and face image 102. An icon 103 representing the location of three-axis reference coil 41 is shown on face image 102 based on the preliminary registration between magnetic tracking system 12 and digitized CT image 48.

For the final registration, professional 20 touches registration probe 16 on several points on the face of subject 14 and signals to system processor 24 to accept these points for subsequent registration calculations. Additionally, in order for these coordinates to represent a minimally distorted surface of skin 52, in one embodiment professional 20 touches with registration probe 16 the skin at bony areas 96 as guided by image 94.

FIG. 7 shows a view 120 on screen 34 during the final, iterative registration, according to an embodiment of the invention. The final iterative registration corresponds to steps 66, 68 and 70 of the flowchart of FIG. 2.

Points 122 on skin 52 of the face of subject 14 indicate the points where professional 20 has touched the face with registration probe 16, typically within areas 96 (colored green). Signals representative of coordinates of points 122 are sent to system processor 24. For the sake of clarity, only a small number of points 122 are shown in FIG. 7. After system processor 24 has received the signals for a number of points, typically 20, it re-calculates the coordinate transformation between the digitized CT image 48 and the points collected by magnetic tracking system 12. After an additional 20 points, system processor 24 again re-calculates the coordinate transformation. By sampling additional points 122 and by collecting the points in bony areas 96, as guided by image 94, professional 20 controls the accuracy of the registration between coordinate frame of reference 46 of magnetic tracking system 12 and digitized CT image 48.

Referring back to the description of the flowchart of FIG. 2, in decision step 70, professional 20 decides whether the registration is sufficiently accurate. For this purpose, professional 20 touches probe 16 on a well-defined location on subject 14, such as a tip of the nose of the subject. Based on his visual observation of an indication of the probe's location on the image of subject 14, professional 20 makes his subjective decision on the achieved registration accuracy.

Figure 8:
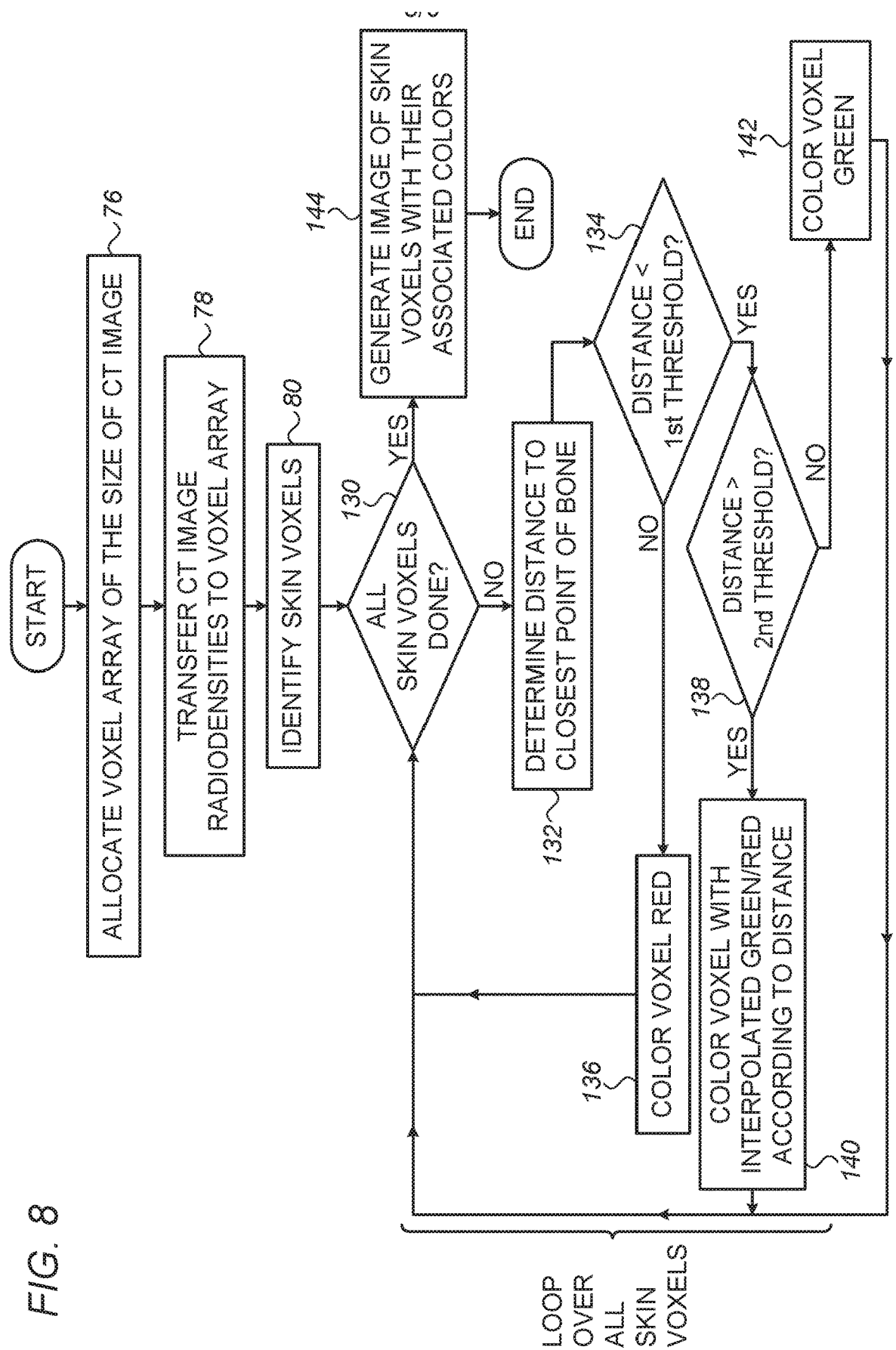
FIG. 8 is a flowchart of the process for rendering an image in an image rendering step, according to an alternative embodiment of the invention.
Figure 9:
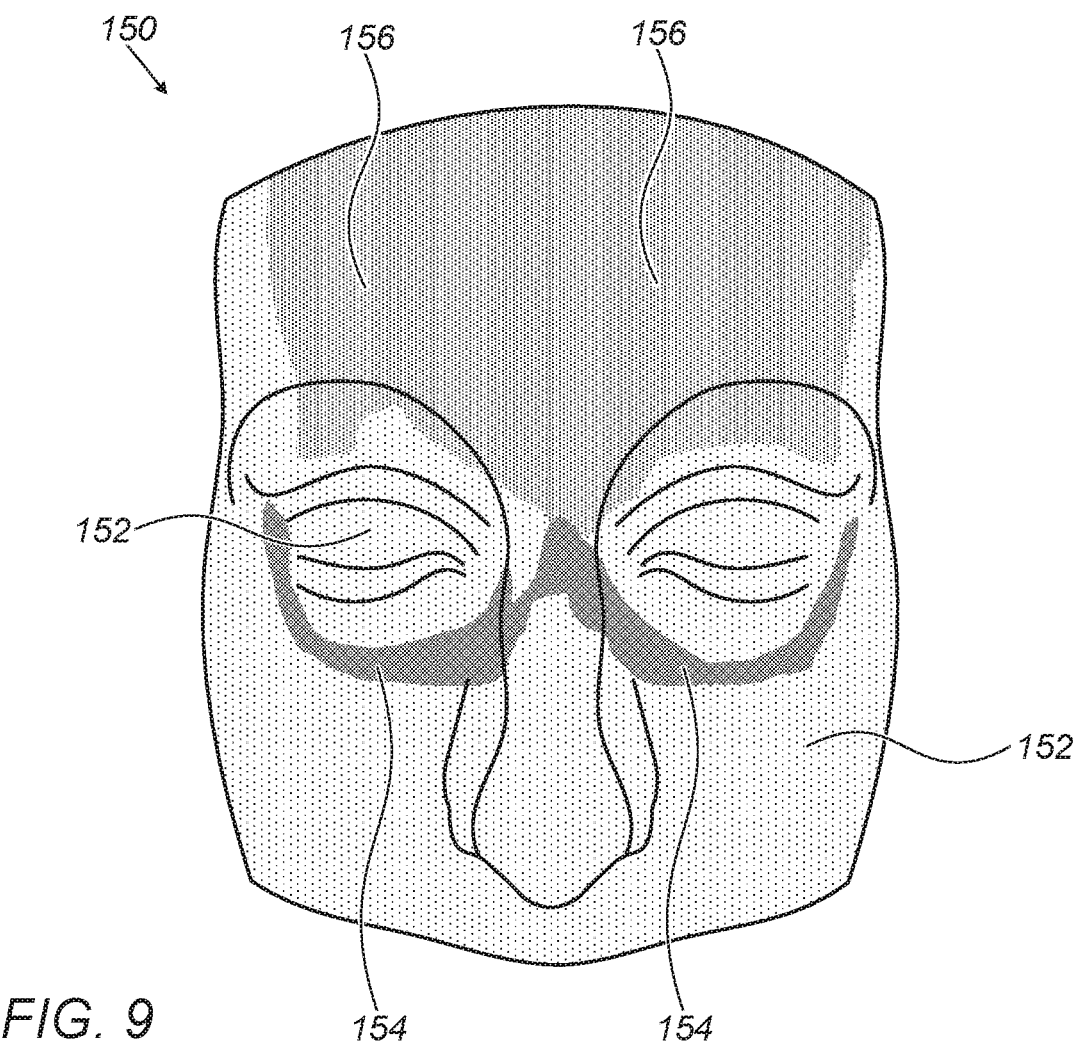
FIG. 9 shows an image indicating the thickness of the soft tissue of the face of a subject, according to the alternative embodiment of the invention.

FIG. 8 is a flowchart of the process for generating an image 150 in image rendering step 62 of FIG. 2, and FIG. 9 schematically illustrates the image, also referred to herein as rendered image 150, according to an alternative embodiment of the invention. The first three steps in the flowchart are substantially identical to those in FIG. 3: system processor 24 allocates in allocation step 76 3-D data array 77 with the same dimensions as digitized CT image 48, and transfers in transfer step 78 the CT image into the data array. As in FIG. 3, each point in data array 77 is called voxel 79. In identification step 80, system processor 24 identifies in data array 77 those voxels 79 associate with skin 52 based on the radiodensities associated with each voxel and its surrounding voxels; as in FIG. 3, these voxels are called "skin voxels" 81.

In steps 130-142 system processor 24 loops over all skin voxels 81, determining in a distance step 132 the distance from the skin voxel to the closest point of underlying bone. In a first comparison step 134, system processor 24 compares the determined distance from skin voxel 81 to the bone to a predetermined first threshold, with the threshold chosen by professional 20 to be typically 10 mm. If the distance is more than the threshold, a red color is associated with skin voxel 81 in red association step 136. In a second comparison step 138, the distance is compared to a predetermined second threshold, with the threshold chosen by professional 20 to be typically between zero and 0.5 mm. If the distance exceeds the second threshold (but, based on first comparison step 134, does not exceed the first threshold), system processor 24 determines in an interpolation step 140 a color based on an interpolated mixture of red and green, based on the ratio of the distances of skin voxel 81 from the first and second thresholds, respectively. Further in interpolation step 140, the resulting mixed color is associated with skin voxel 81. If, in second comparison step 138, system processor 24 determines that the distance is less than or equal to the second threshold, a green color is associated by the system processor to skin voxel 81 in a green association step 142. Once system processor 24 has looped through all skin voxels 81, the process ends by the system processor generating an image of skin voxels 81 with their associated colors in image generation step 144.

FIG. 9 shows image 150 indicating the thickness of the soft tissue of the face of subject 14, according to the alternative embodiment of the invention.

Similarly to FIG. 4, in preparation for the registration between magnetic tracking system 12 and digitized CT image 48, system processor 24 renders image 150 indicating the thickness of the soft tissue, as described below. In the embodiment described hereinbelow the visual coding is based on different colors.

As described above for the flowchart of FIG. 8, system processor 24 identifies in digitized CT image 48 skin voxels 81. For each skin voxel 81, system processor 24 segments CT image 48 to identify bony material of the subject and measures distances from skin 52 to underlying bone. System processor 24 determines the color of each skin voxel 81 as follows: if the distance exceeds a predetermined first threshold, typically 10 mm, the skin voxel is colored red. If the distance doesn't exceed a predetermined second threshold, typically 0-0.5 mm, skin voxel 81 is colored green. If the distance exceeds the second threshold but does not exceed the first threshold, skin voxel 81 is colored with a mixture of green and red, wherein the relative quantities of red and green are based on the relative distance of the skin voxel from the first and second thresholds, respectively. The colors green, red, and mixed color are represented in FIG. 9 by different shadings, such as in areas 154, 152, and 156, respectively. Thus, in image 150, areas 154 are bony areas where the thickness of the soft tissue less or equal to the second threshold, areas 152 are fleshy areas where the thickness of the soft tissue exceed the first threshold, and areas 156 are areas where the thickness of the soft tissue is between the two thresholds. In areas 156, the relative "greenness" and "redness" indicate the relative "distance" of each voxel to the two thresholds.

In the alternative embodiment described in FIGS. 8-9, image 150 is used to replace image 94 in FIGS. 6-7. Professional 20 is now guided by image 150 to touch with registration probe 16 the skin at bony areas 154, and possibly in those parts of areas 156, where the color indicates that the soft tissue is thin.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method comprising:
   (a) receiving a computerized tomography (CT) image of a body part of a subject, the image comprising a plurality of voxels, wherein each of the plurality of voxels is associated with a density;
   (b) segmenting the image so as to identify a plurality of skin voxels associated with a surface of a skin and a plurality of bone voxels associated with a surface of a bone in the image;
   (c) for each of the plurality of skin voxels, measuring respective minimum distances to an underlying bone voxel of the plurality of bone voxels;
   (d) rendering an image of the surface of the skin while visually coding the rendered image so as to indicate the respective minimum distances of each of the plurality of skin voxels;
   (e) selecting a plurality of locations on the body part of the subject based on the visual coding of the rendered image; and
   (f) using a registration probe to add registration points by touching the plurality of locations on the body part of the subject.

2. The method according to claim 1, wherein visually coding the rendered image comprises applying a first image characteristic to first areas of the skin where the minimum distance does not exceed a predetermined threshold, and applying a second image characteristic to second areas of the skin wherein the minimum distance exceeds the predetermined threshold, the method further comprising selecting the plurality of locations on the body part from the first areas of the skin having the first image characteristic.

3. The method according to claim 2, wherein the first and second image characteristics are two distinguishable colors.

4. The method according to claim 1, wherein visually coding the rendered image comprises applying the first image characteristic to the first areas of the image of the surface of the skin where the minimum distance does not exceed a predetermined first threshold, applying the second image characteristic to the second areas of the image of the surface of the skin wherein the minimum distance exceeds a predetermined second threshold, and applying a third image characteristic to third areas of the image of the surface of the skin wherein the minimum distance does not exceed the first threshold but exceeds the second threshold, the method further comprising selecting the plurality of locations on the body part while giving priority to the first areas over the third areas, and giving priority to the third areas over the second areas.

5. The method according to claim 4, wherein the first, second, and third image characteristics are three distinguishable colors.

6. The method according to claim 5, wherein the color of the third image characteristic is a combination of the colors of the first and second image characteristics, and wherein relative weights of the first and second colors in the combination are determined from a ratio of a first difference to a second difference, wherein the first difference is a difference between the first threshold and the minimum distance, and the second difference is a difference between the minimum distance and the second threshold.

7. The method according to claim 4, wherein the first and second image characteristics are two distinguishable graylevels, and the third image characteristic is a third graylevel, wherein the third graylevel is an interpolated graylevel between the graylevels of the first and second image characteristic, wherein the interpolated graylevel is determined by differences between the minimum distance and the first and second thresholds, respectively.

8. The method according to claim 1, wherein the body part comprises a head.

9. The method according to claim 1, wherein the minimum distance for each of the plurality of skin voxels is established along a normal to the surface of the corresponding underlying bone voxel.

10. An apparatus comprising:
(a) a display device; and
(b) a processor, which is configured to:
  (i) receive a computerized tomography (CT) image of a body part of a subject, the image comprising a plurality of voxels, wherein each of the plurality of voxels is associated with a density,
  (ii) segment the image so as to identify a plurality of skin voxels associated with a surface of a skin and a plurality of bone voxels associated with a surface of a bone in the image,
  (iii) for each of the plurality of skin voxels, measure respective minimum distances to an underlying bone voxel of the plurality of bone voxels,
  (iv) render an image of the surface of the skin on the display device while visually coding the rendered image so as to indicate the respective minimum distances of each of the plurality of skin voxels, wherein the visual coding of the rendered image comprises a first image characteristic for first areas of the skin and a second image characteristic for second areas of the skin,
  (v) receive data from a registration probe indicating a plurality of locations on the body part of the subject, wherein the plurality of locations are within the first areas of the skin, and
  (vi) add registration points based on the data from the registration probe.

11. The apparatus according to claim 10, wherein visually coding the image comprises applying the first image characteristic to the first areas of the skin where the minimum distance does not exceed a predetermined threshold, and applying the second image characteristic to the second areas of the skin wherein the minimum distance exceeds the predetermined threshold.

12. The apparatus according to claim 11, wherein the first and second image characteristics are two distinguishable colors.

13. The apparatus according to claim 11, wherein the first and second image characteristics are two distinguishable patterns.

14. The apparatus according to claim 11, wherein the first and second image characteristics are two distinguishable graylevels.

15. The apparatus according to claim 10, visually coding the rendered image comprises applying the first image characteristic to the first areas of the image of the surface of the skin where the minimum distance does not exceed a predetermined first threshold, applying the second image characteristic to the second areas of the image of the surface of the skin wherein the minimum distance exceeds a predetermined second threshold, and applying a third image characteristic to third areas of the image of the surface of the skin wherein the minimum distance does not exceed the first threshold but exceeds the second threshold, the method further comprising selecting the plurality of locations on the body part while giving priority to the first areas over the third areas, and giving priority to the third areas over the second areas.

16. The apparatus according to claim 15, wherein the first, second, and third image characteristics are three distinguishable colors.

17. The apparatus according to claim 16, wherein the color of the third image characteristic is a combination of the colors of the first and second image characteristics, and wherein relative weights of the first and second colors in the combination are determined from a ratio of a first difference to a second difference, wherein the first difference is a difference between the first threshold and the minimum distance, and the second difference is a difference between the minimum distance and the second threshold.

18. The apparatus according to claim 15, wherein the first and second image characteristics are two distinguishable graylevels, and the third image characteristic is a third graylevel, wherein the third graylevel is an interpolated graylevel between the graylevels of the first and second image characteristic, wherein the interpolated graylevel is determined by differences between the minimum distance and the first and second thresholds, respectively.

19. The apparatus according to claim 10, wherein the minimum distance for each of the plurality of skin voxels is established along a normal to the surface of the corresponding underlying bone voxel.

20. The apparatus according to claim 10, wherein the body part comprises a head.

21. A computer software product, comprising a non-transitory computer-readable medium in which program instructions are stored, which instructions, when read by a computer, cause the computer to:
(a) receive a computerized tomography (CT) image of a body part of a subject, the image comprising a plurality of voxels, wherein each of the plurality of voxels is associated with a density;
(b) segment the image so as to identify a plurality of skin voxels associated with a surface of a skin and a plurality of bone voxels associated with a surface of a bone in the image;
(c) for each of the plurality of skin voxels, measure respective minimum distances to an underlying bone voxel of the plurality of bone voxels;
(d) render an image of the surface of the skin while visually coding the rendered image so as to indicate the respective minimum distances of each of the plurality of skin voxels, wherein the visual coding of the rendered image comprises a first image characteristic for first areas of the skin and a second image characteristic for second areas of the skin;
(e) receive data from a registration probe indicating a plurality of locations on the body part of the subject, wherein the plurality of locations are within the first areas of the skins; and (vi) add registration points based on the data from the registration probe.

\* \* \* \* \*